United States Patent [19]

Ozeki et al.

[11] Patent Number: 4,674,046
[45] Date of Patent: Jun. 16, 1987

[54] METHOD AND APPARATUS FOR OBTAINING THREE DIMENSIONAL TOMOGRAPHIC IMAGES BY INTERPOLATION OF A PLURALITY OF PROJECTION SLICE DATA BIND FOR OBTAINING PROJECTION DATA FOR A CHOSEN SLICE

[75] Inventors: Takeshi Ozeki; Shinichi Tsubura, both of Ootawara, Japan

[73] Assignee: Kabushiki Kaisha Toshiba, Kawasaki, Japan

[21] Appl. No.: 692,559

[22] Filed: Jan. 18, 1985

[30] Foreign Application Priority Data

Jan. 23, 1984 [JP] Japan .................................. 59-9759

[51] Int. Cl.$^4$ ............................................. G06F 15/42
[52] U.S. Cl. .................... 364/414; 378/901; 364/522
[58] Field of Search ....................... 364/414, 521, 522; 378/901; 382/46

[56] References Cited

U.S. PATENT DOCUMENTS

| | | | |
|---|---|---|---|
| 3,621,214 | 11/1971 | Romney ..................... | 235/151 |
| 4,174,481 | 11/1979 | Liebetruth .................. | 250/445 T |
| 4,418,387 | 11/1983 | Yamaguchi ................. | 378/901 |
| 4,422,146 | 12/1983 | Yamaguchi ................. | 378/901 |

OTHER PUBLICATIONS

IBM Technical Disclosure Bulletin, vol. 27, No. 7A, Dec. 1984, pp. 4026–4027.

Primary Examiner—Jerry Smith
Assistant Examiner—G. Hayes
Attorney, Agent, or Firm—Finnegan, Henderson, Farabow, Garrett & Dunner

[57] ABSTRACT

According to a scan planning method for obtaining any tomographic image by a CT system, projection data of a plurality of parallel slices is acquired by a computed tomographic scanning device. The tomographic images are interpolated in accordance with the tomographic data of the slices which is obtained by the CT scanning device thereby providing the three-dimensional image data. A three-dimensional object image is then displayed on a display in accordance with the three-dimensional image data. A viewpoint for the object image changes, and an orientation angle of the object image changes in accordance with a manually input coordinate information. A slice position image representing the designated position and angle of the slice is displayed three-dimensionally in accordance with the coordinate information. The CT scanning device is controlled in accordance with the position and angle of the slice position image with respect to the object image.

15 Claims, 20 Drawing Figures

F I G. 13A     F I G. 13B
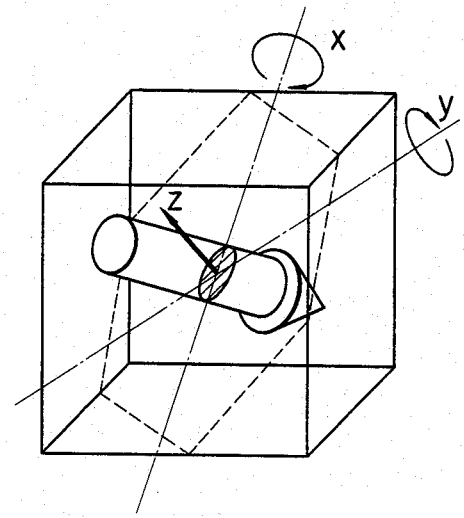
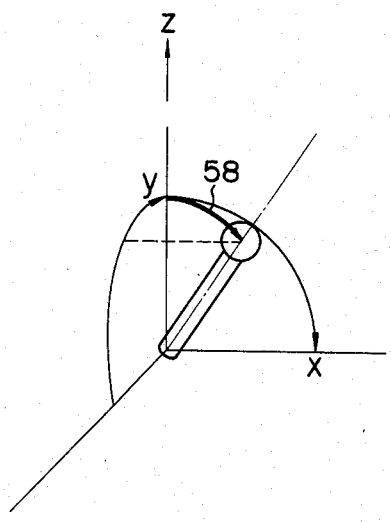
F I G. 14
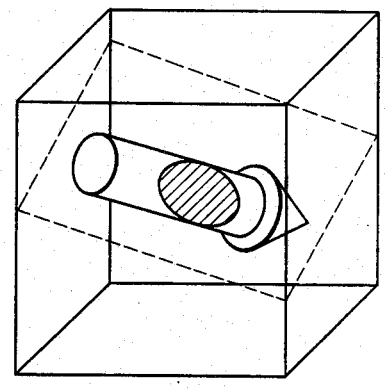

METHOD AND APPARATUS FOR OBTAINING THREE DIMENSIONAL TOMOGRAPHIC IMAGES BY INTERPOLATION OF A PLURALITY OF PROJECTION SLICE DATA BIND FOR OBTAINING PROJECTION DATA FOR A CHOSEN SLICE

BACKGROUND OF THE INVENTION

The present invention relates to an imaging technique mainly used in medical diagnosis and, more particularly, to a method and apparatus for planning image scanning so as to obtain any tomographic image in any CT (computed tomograph) system, e.g., an MRI (magnetic resonance imaging) system, an X-ray CT system, an emission CT system, and an ultrasonic CT system for forming an image by utilizing an MR (magnetic resonance) phenomenon, radiation or ultrasonic waves in accordance with CT techniques.

A new age for medical diagnosis has been ushered in by the development and progress of X-ray CT systems. In a conventional X-ray (fluoroscopic) picture, one-dimensional information along the X-ray radiation direction is superposed to obtain a two-dimensional image (images corresponding to the depth of an examined portion cannot be obtained) in which the resolution of the one-dimensional image has been substantially lost. However, in an X-ray CT image, a minimum range in depth of an examined object represented by a two-dimensional image can be set to provide a slice, thereby obtaining an image having a one-dimensional resolution along the direction of depth. In earlier developed X-ray CT systems, only a cross-sectional tomographic image is obtained. However, in recent X-ray CT systems, any tomographic image at any angle with respect to the object can be obtained by changing the relative angle between the gantry (X-ray scanning unit) and an object to be examined.

The X-ray CT image is based upon examination of the coefficient X-ray absorption. In addition to the X-ray CT image, an MRI system has been recently developed which can obtain an image based on MR phenomenon information. In MRI systems of the present, slices at any direction can be obtained, and further developments are expected in the future.

As a CT application, an emission CT is proposed wherein image reconstruction is performed in accordance with transmission/absorption information obtained such that radiation is emitted from a radiation source such as a radioisotope to the object to be examined, and that the radiation is detected around the object. Another CT application is exemplified by an ultrasonic CT technique wherein transmission/absorption information obtained by projecting an ultrasonic wave is used to reconstruct a CT image. These CT techniques have been developed and applied in practice.

A scan planning system is proposed as a conventional X-ray CT system to photograph a slice at a proper position. A typical example of the scan planning system is described in U.S. Pat. No. 4,174,481. In such an X-ray CT scan planning system, an X-ray tube and an X-ray detector are moved together along an axis of an object to be examined to obtain a so-called scano-image which consists of one-directional projection images to form a two-dimensional image of the object. An operator designates a desired slice position with respect to the scano-image. Photographing (projection data acquisition) is performed at the designated position.

However, this system is based upon a CT system for obtaining slice images which are parallel to each other and which are perpendicular to the axis of the object. Therefore, a slice cannot be obtained at any angle and any position. (A tilted slice cannot be designated in the scano-image along the projection direction).

There is no scan planning system for obtaining any slice in the same manner as in the conventional MRI system.

When an image is scanned in the MRI system, a portion subjected to image scanning is roughly determined and several images are obtained in the vicinity of the portion at different conditions. Thereafter, a desired image is selected among a plurality of resultant images. As a result, many pictures are wasted, and repeated photographing imposes a mental and physical strain on the patient being examined.

In the scan planning system described in U.S. Pat. No. 4,174,481, a cross-sectional slice is designated. In this case, in order to obtain a tomographic image of a slice at any angle and any position in the X-ray CT system, a plurality of tomographic images are obtained and are subjected to image processing for image conversion. A desired tomographic image at a desired direction is reconstructed by interpolation. Since the resultant image is reconstructed by interpolation, its resolution is inevitably degraded. Furthermore, in the MRI system, in order to obtain a scano-image as a DR (digital radiography) constituting an image such as a normal X-ray image, a plurality of slice data must be obtained, and the scano-image is constructed by reproduction in accordance with the slice data even in a simplest case. In addition, since any slice can be photographed in the MRI system, a proper slice cannot be selected in an image such as a scano-image having a predetermined direction. Therefore, in order to accurately select a proper slice, an optimal slice is desirable determined in accordance with a plurality of images taken from different angles.

SUMMARY OF THE INVENTION

It is an object of the present invention to provide a simple method and apparatus for easily planning a scanning, wherein images taken from different angles are displayed, slices of different orientations can be set on the screen, and a desired slice can be easily selected when scan planning is made to obtain any tomographic image in the CT system.

According to a scan planning method of the present invention, a tomographic image at any slice can be obtained in the CT system in the following manner.

In a CT image scanning device for acquiring projection data along a predetermined slice of an object to be examined in different directions and for reconstructing a CT image, i.e., a tomographic image, projection data for a plurality of parallel slices of the object are collected. The tomographic images of a two-dimensional image data for a plurality of slices which are obtained by the CT image scanning device in accordance with the data acquisition are interpolated to obtain a three-dimensional image data of a region defined by two outermost slices. The object image is displayed three-dimensionally in accordance with the three-dimensional image data. A viewpoint (an angle of the displayed image) changes in accordance with externally entered first coordinate information. In addition, a slice position image representing a slice at a displayed position and an angle is three-dimensionally superposed on the image of the object in accordance with externally entered second coordinate information. Simultaneously, the CT image scanning device is controlled in accordance with information which controls a display of the slice position image and the object image. Projection data of a slice which represents the position and angle of the slice position image corresponding to the object image is acquired. As a result, a tomographic image is reconstructed in accordance with the projection data.

A scan planning apparatus according to the present invention comprises: a CT image scanning device for acquiring projection data of a predetermined slice of an object along a plurality of directions and for reconstructing a CT image; means for controlling the CT image scanning device to cause the CT image scanning device to acquire the projection data of a plurality of parallel slices of the object and to pick up tomographic images of the plurality of slices; means for interpolating a plurality of tomographic images obtained by the CT image scanning device to obtain a three-dimensional image data of a region defined by two outermost slices of the plurality of slices; means for forming an object image for three-dimensionally displaying the object in accordance with the three-dimensional image data obtained by the interpolating means and for displaying the object image; a coordinate information input device for externally entering coordinate information; means for changing a viewpoint (an angle of the displayed object image) of the object image in accordance with coordinate information entered by the coordinate information input device; means for superposing on the object image a slice position image of a slice having a position and an angle which are designated by the coordinate information entered by the coordinate information input device, thereby three-dimensionally displaying the slice position image; and means for controlling the CT image scanning device to cause the CT image scanning device to acquire projection data for a slice corresponding to the displayed slice position image, and for reconstructing a tomographic image corresponding to the slice represented by the projection data.

According to the scan planning method and apparatus for obtaining any tomographic image in the CT system, slices at different orientations are observed on the screen so as to allow a proper slice to be easily selected.

BRIEF DESCRIPTION OF THE DRAWINGS

FIGS. 11A, 12A, 13A and 14 are schematic representations of displayed images to be referred to in the description of the operation of the apparatus shown in FIG. 2, respectively;

FIGS. 11B, 12B and 13B are schematic representations for explaining the operation of the apparatus shown in FIG. 2, and the input operation associated with the images shown in FIGS. 11A, 12A and 13A.

DETAILED DESCRIPTION OF THE PREFERRED EMBODIMENT

Slice setting as a main operation in a preferred embodiment will be briefly described. In this embodiment, the present invention is applied to an MRI (magnetic resonance imaging) system. In this case, a CT image scanning device comprises an MRI scanning system.

Figure 1:
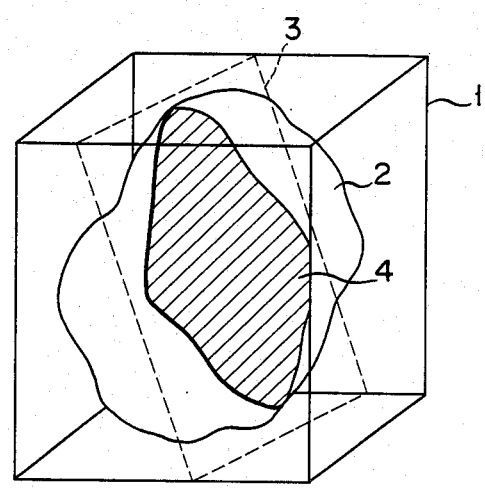
FIG. 1 is a schematic representation of a displayed image when a slice is set in a scan planning system which adapts the present invention.

FIG. 1 shows an image displayed on a display such as a CRT (cathode-ray tube). As indicated by auxiliary lines 1, an object image 2 is three-dimensionally displayed by projecting image information obtained by observing the object from different positions. A slice position image 3 showing a slice position is superposed on the object image. A slice image 4 is also displayed on the display. The slice image 4 shows a plane of the object. In this case, a slice of an ROI (region of interest) is determined in accordance with an SROI (surface region of interest) which is displayed as the slice position image 3. The slice can be arbitrarily set in accordance with a PROI (point region of interest) for defining a point included in the slice, an LSOI (line segment of interest) for defining a line segment included in the slice, a CROI (circular region of interest) defining a circular region included in the slice, an FROI (free region of interest) defining a free surface having a free shape, or a combination thereof. The position and size of elements for setting the slice may change. When the slice is set in accordance with the SROI, the MRI system as a scanning device starts acquiring slice data in accordance with scan planning represented by the slice position image 3, and a detailed description thereof will be made later with reference to FIGS. 3A and 3B.

Figure 2:
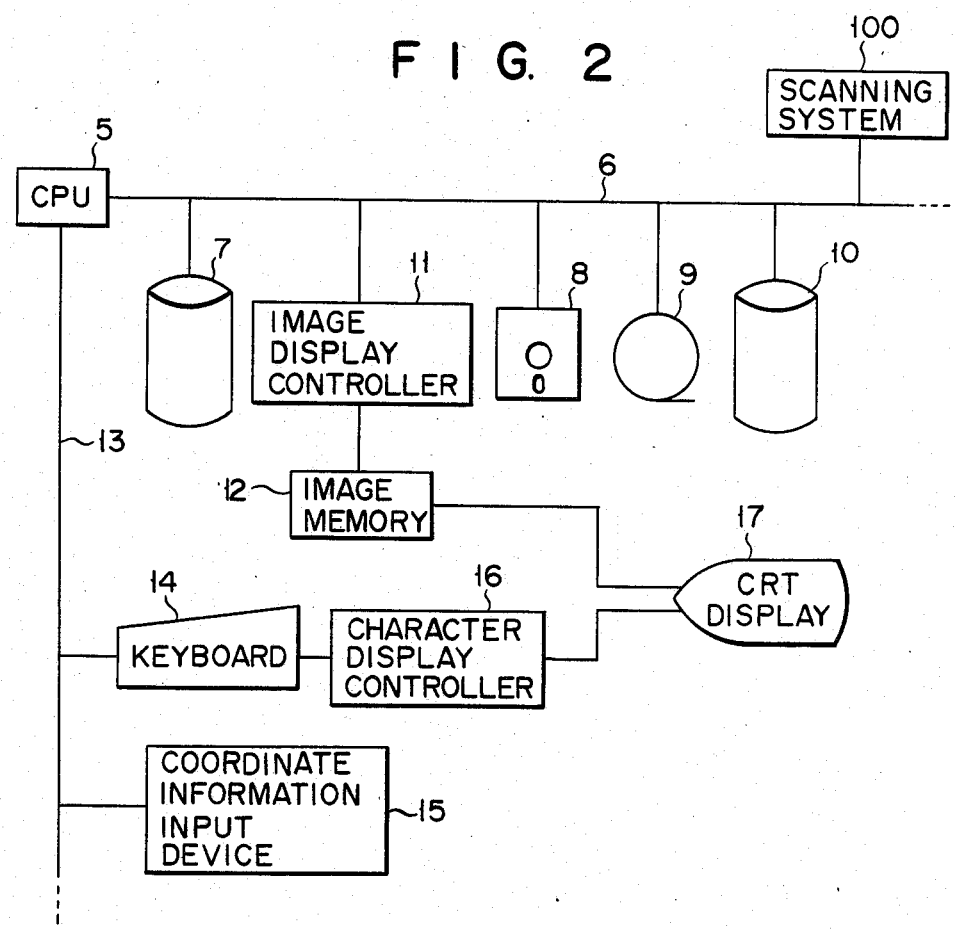
FIG. 2 is a block diagram showing a scan planning apparatus according to an embodiment of the present invention.

The main arrangement of the apparatus of this embodiment is illustrated in FIG. 2.

A CPU (central processing unit) 5 is connected to storage devices through a DMA (direct memory access) bus 6. The storage devices are a magnetic disk unit 7, a floppy disk unit 8, a magnetic tape unit 9 and an optical disk unit 10. A scanning system 100 is connected to the DMA bus 6 to cause the system 100 to acquire MR (magnetic resonance) projection data of the object. The projection data obtained by the scanning system 100 is processed by the CPU 5 (or a processor, not shown, connected to the CPU 5) so as to perform image reconstruction. The reconstructed tomographic image is stored in the storage devises. An image display controller 11 is connected to the CPU 5 through the DMA bus 6. An image memory 12 and a CRT display 17 are connected to the image display controller 11. A keyboard 14 and a coordinate information input device 15 such as a track ball, a joystick or a mouse are connected to the CPU 5 through an I/0 (input/output) bus 13. A character display controller 16 is connected to the keyboard 14. The character display controller 16 is also connected to a CRT display 17. At least one of the controllers 11 and 16 is controlled in response to a key input and/or a coordinate information input from the keyboard 14 and/or the coordinate information input device 15, thereby performing data transfer between the respective components. As a result, the object image 2 and the ROI setting tomographic image 3 are displayed three-dimensionally on the CRT display 17. Similarly, at least one of the image display controllers 11 and 16 is controlled in response to a key input and/or a coordinate information input from the keyboard 14 and/or the coordinate information input device 15, thereby changing the orientation of the object image 2 and the position and orientation of the ROI setting slice position image 3. As a result, a slice is set.

The operation of the system described above will be described in detail with reference to the flow chart in FIGS. 3A and 3B.

The apparatus of the present invention comprises a interactive system, i.e., a system between an operator and a machine.

Figure 3A:
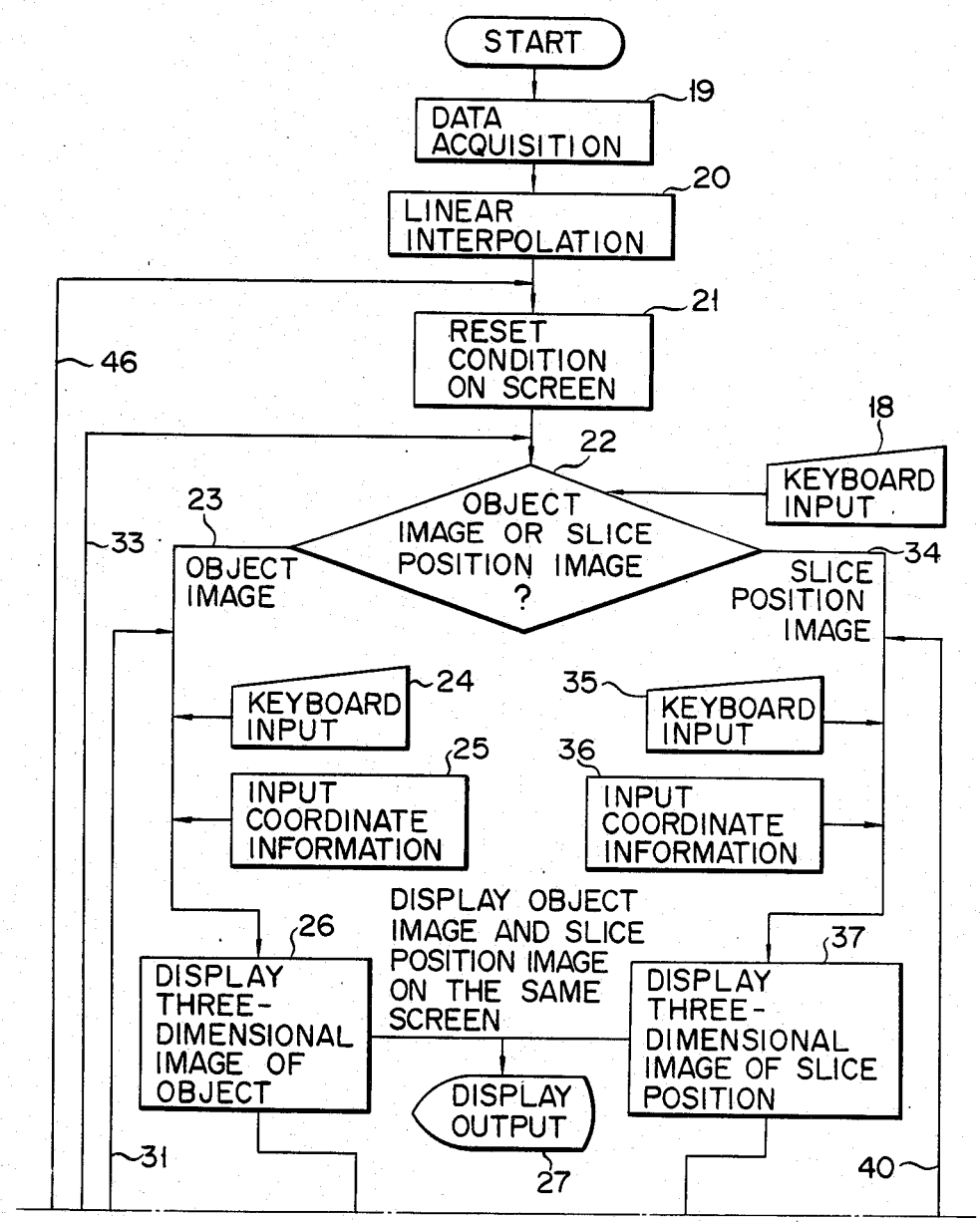
FIGS. 3A and 3B are flow charts for explaining the operation of the scan planning apparatus shown in FIG. 2.
Figure 3B:
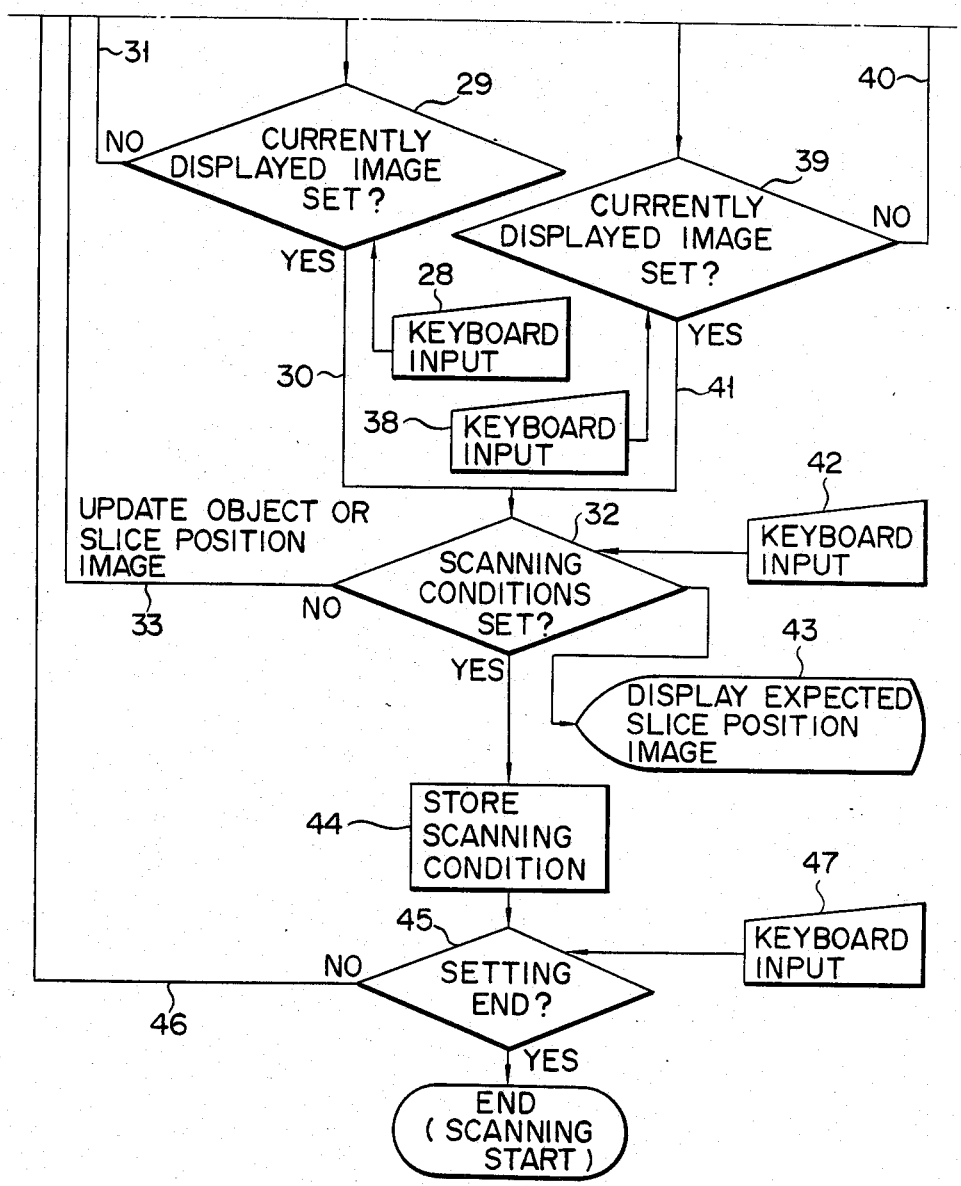

Referring to FIGS. 3A and 3B, when the operation is started, slice data for a plurality of parallel slices spaced at a relatively large interval (the interval need not be large, but can be large in practice) are acquired by the scanning system 100 (step 19). Linear interpolation is performed for the respective slices in accordance with a plurality of resultant parallel slice data (step 20), thereby obtaining the three-dimensional image data.

Figure 4:
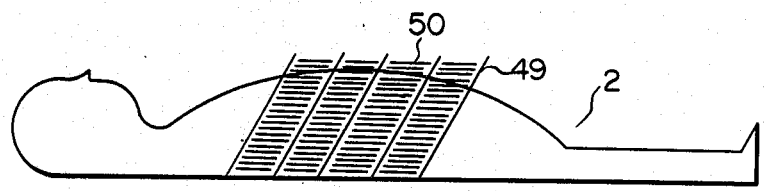
FIG. 4 is a schematic representation of a slice of the object which is referred to in the description of the operation of the apparatus shown in FIG. 2.

As shown in FIG. 4, tomographic images are obtained for the plurality of parallel slices 49 spaced at a relatively large interval along a predetermined direction. In order to obtain information between the slices 49 which cannot be obtained by data acquisition of the parallel slices, linear interpolation is performed in accordance with the image data of the slices 49. Interpolated data about intermediate portions 50 between the slices 49 are used to obtain a three-dimensional object image data which is then stored in a memory.

Referring back to FIGS. 3A and 3B, after the three-dimensional image data of the object is obtained, the slice scanning conditions on the display are reset (step 21). In this step, the previous conditions are cleared to initialize the display system. The operator enters data (18) at the keyboard 14 as to whether or not the object image or the slice position image is processed (controlled and finally set) (decision step 22). In the first selection, a route (23) for setting the object image is normally selected. Three-dimensional display processing using the resultant three-dimensional image data is performed (step 26), and the three-dimensional image of the object is displayed on the CRT display 17 (display output step 27). In the initial state, information designating changes in a display angle of the object image is not entered as an input (24) at the keyboard 14 and/or an input (25) at the coordinate information input device 15. An angle of the object image is set to define a viewpoint as a reference front surface of the object image. The object image from the front viewpoint is displayed. The operator enters an input (28) at the keyboard 14 so as to determine whether or not the object image in this state is set (decision step 29). When the operator does not enter the input (28), the flow repeatedly advances to a route (31) to fetch the input (24) at the keyboard 14 and the input (25) at the coordinate information input device 15. By repeating the input (24) at the keyboard 14 and-/or the input (25) at the coordinate information input device 15, information is entered to change the viewpoint of the object image. In other words, information is entered to change the display angle of the object image. When display angle change information is entered, three-dimensional display processing (26) using the three-dimensional image data and display output processing for the CRT display 17 are performed (step 27). Therefore, the three-dimensional output image at a display angle (viewpoint) corresponding to the designated information is displayed on the CRT display 17 (display output step 27). The operator enters an input (28) at the keyboard so as to determine whether or not the object image in the displayed state is set (decision step 29). When the display state need not be changed, a corresponding setting input is entered and the flow advances to step (32) through a route (30). However, unless the display image setting command is entered as a keyboard input (28), the flow advances through the route (31). Every time the viewpoint changes, the displayed image changes while the changing image is continuously displayed.

When the object image is set, the CPU checks (decision step 32) whether or not the scanning conditions of the scanning system 100 are set in accordance with the displayed object and slice position images. In the case where the slice position image is not set, the flow advances through a route (33) and returns to decision step (22) so as to determine whether the object image or the slice position image is selected.

The operator then enters data representing that the slice position image is processed (controlled and set), and thus the flow advances through a route (34). The position and orientation of the slice (image) are designated by an input (35) at the keyboard 14 and an input (36) at the coordinate information input device 15 in the same manner as in the object image processing. Three-dimensional display processing is performed in accordance with these inputs (step 37). The slice position image is displayed on the CRT display 17 (display output step 27). The preset slice position image is oriented toward the front until the operator input other data. The slice position image is superposed on the three-dimensional object image in the CRT display 17. The operator can change the image to designate a slice while observing the three-dimensional image displayed on the CRT display 17. The operator enters an input (38) at the keyboard 14 so as to determine whether or not the displayed slice position image can be set (decision step 39). In decision step (39), the input (35) at the keyboard 14 and the input (36) at the coordinate information input device 15, and three-dimensional display processing (37) are repeated through a route (40) until a slice position image setting command is entered. The operator can operate the keyboard 14 and the coordinate information input device 15 while he observes the image displayed on the CRT display 17. As a result, the position and orientation of the displayed slice position image can change in response to the inputs (35) and (36).

When the slice position image setting command is entered in decision step (39), the flow advances through a route (41). The CPU then checks (decision step 32) again whether or not the scanning conditions of the MRI system can be set in accordance with the displayed object and slice position images. When the scanning conditions setting command is entered as the input (42) at the keyboard 14, the flow advances to the next step (44). In decision step (32), when the operator enters a command for changing the setting conditions of the displayed object image and the displayed slice position image, the flow returns to decision step (22) through the route (33), and the same operation as described above is repeated. However, in the decision step (32), when the input (42) is entered at the keyboard 14, an expected slice position image is interpolated in accordance with the three-dimensional image data and is displayed (display output step 43).

When the scanning condition setting command is entered in the decision step (32), necessary scanning condition data (including the scanning number to be described later) of a slice corresponding to the displayed slice position image is stored (step 44). The CPU checks (decision step 45) whether or not all the slices are designated. In other words, the CPU checks whether or not the input (47) is entered at the keyboard 14. In order to designate another slice, a corresponding input (47) is entered, and the flow advances through a route (46) and returns to the step (21). In this step, the setting conditions displayed on the display are reset. This slice is designated in the same manner as described above.

In the decision step (22), the slice (slice position image) can be specified instead of specifying the object image, and the object image can be three-dimensionally moved on the screen, thereby designating the slice. When the keyboard input (47) at the time of setting a designation of all slices (decision step 45) represents an end of slice designation, the processing of this system is completed, and the scanning system 100 scans (projection and scanning) the object to be examined in accordance with the set conditions.

Displayed images are illustrated in FIGS. 5 to 8 where the object image is three-dimensionally displayed and its orientation (viewpoint) is set. The three-dimensional object image comprises three-dimensional data consisting of a set of tomographic images. Assume that the image data are displayed as a three-dimensional image in an overlapping manner. In this case, the respective data are added to form a three-dimensional image, and a transmission image is obtained. However, when data representing a rear portion is masked by data representing a front portion, a nontransmission image is obtained. When a transmission image is used to constitute a three-dimensional object image, a positional relationship between internal tissue of an object such as an internal organ is clarified. Therefore, the transmission and nontransmission images are selectively used, or are superposed to obtain a transmission image whose edge is emphasized by the nontransmission image. However, of course, the transmission and nontransmission images can be separately used.

An object image 51 is illustrated wherein a conical portion corresponds to the head of a patient.

Figure 5:
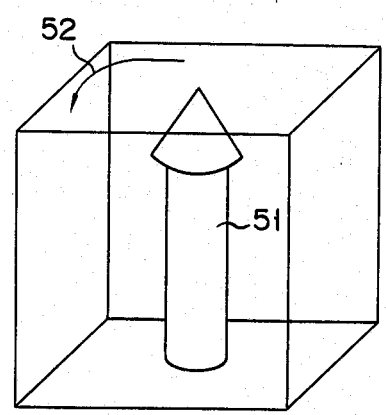
FIGS. 5 to 8 are schematic representations of displayed images to be referred to in the description of the operation of the apparatus shown in FIG. 2, respectively.
Figure 6:
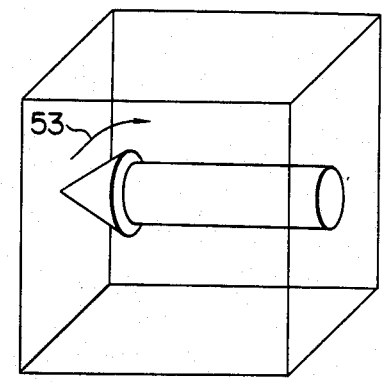
Figure 7:
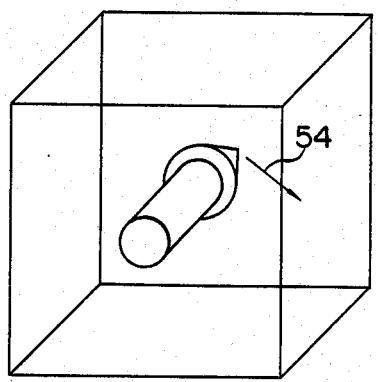

Assume that the initial image is given in FIG. 5. Unless the object image is set, the system processing is looped through the route (31) in FIGS. 3A and 3B. When the operator enters an input at the coordinate information input device 15, the changing image is continuously displayed in accordance with the changing viewpoint. In other words, the changing image is displayed like a moving image. A case will be described wherein a track ball is used as the coordinate information input device 15. When the track ball is rotated in the direction indicated by arrow 52, the object image 51 is rotated on the screen and is oriented as an image shown in FIG. 6. When the viewpoint changes in response to the input (25) at the coordinate information input device 15, the input preferably designates the moving direction of the object image (but not the moving direction of the viewpoint). This is because a coincidence of the operating direction and the moving direction of the image generally improves operability. When the track ball is rotated in the direction given by arrow 53, the image in FIG. 6 is rotated to obtain an image in FIG. 7. Furthermore, when the track ball is rotated in the direction of arrow 54, the image in FIG. 7 is rotated to obtain an image in FIG. 8. It is possible to rotate the image of FIG. 5 to directly obtain the image in FIG. 8. For this purpose, the coordinate information input device must comprise a three-dimensional input device such as a track ball. In this embodiment, the viewpoint is finally set to obtain the image in FIG. 8.

Figure 8:
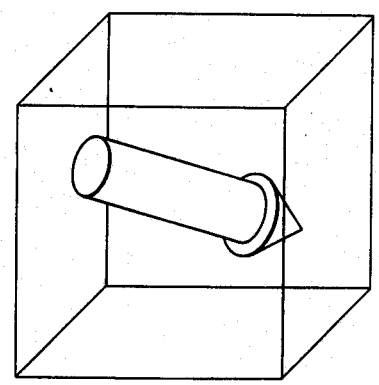

A case will be described with reference to FIGS. 9 to 14 wherein a slice position is set when the object image is oriented as shown in FIG. 8.

Setting and updating of the slice position is performed by using a three-dimensional joystick as the coordinate information input device 15. A normal joystick is used to input two-dimensional coordinate information. For this purpose, this joystick is tilted in the back-and-forth and right-and-left directions. However, in addition to these directions, a three-dimensional joystick is also moved along an axial direction of the stick. Furthermore, movement along the axial direction is used to enter three-dimensional coordinate information.

Figure 9:
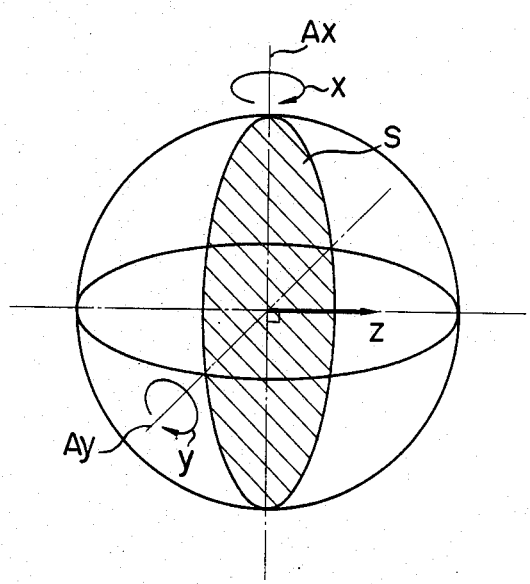
FIGS. 9 and 10 are, respectively, schematic representations for explaining a coordinate information input section in the apparatus shown in FIG. 2.
Figure 10:
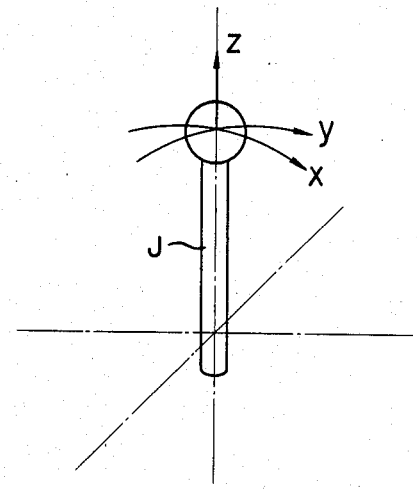

When the three-dimensional joystick J shown in FIG. 10 is inclined in the x direction or the y direction or is moved along the z direction, corresponding coordinate information is entered such that a slice S in FIG. 9 is pivoted with respect to the Ax-axis or the Ay-axis, or is linearly moved along the vertical direction.

Figure 11A:
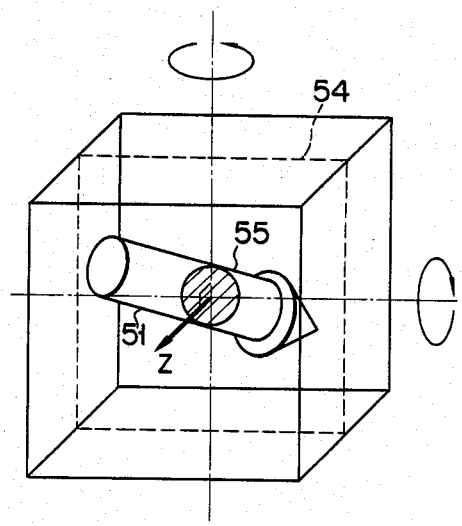
Figure 11B:
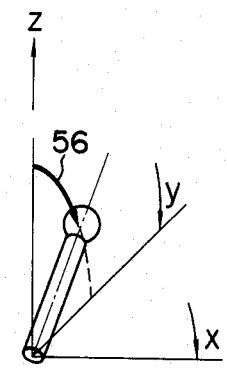
Figure 12A:
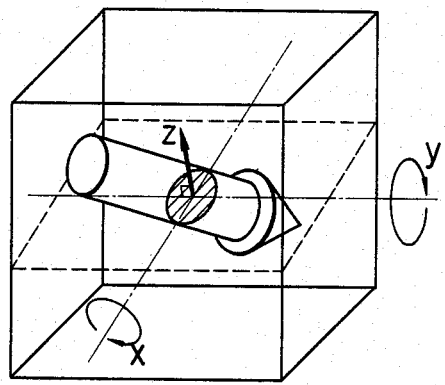
Figure 12B:
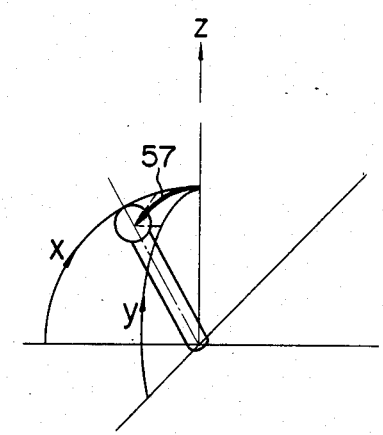

Since the orientation of the object image 51 is set on the display screen, as shown in FIG. 8, a slice position image 54 is illustrated, as shown in FIG. 11A. When a predetermined command is entered, a slice image 55 of a slice corresponding to the slice position image 54 is also displayed. The slice image 55 is displayed as a transmission image in the object image 51. In this state, when the joystick J is moved in the x, y and z directions in FIG. 10, the slice position image can be continuously moved along the x, y and z directions in FIG. 9. The object image 51 is already fixed and will not move. Only the slice position image 54 is moved. When the joystick J is moved in the direction indicated by arrow 56 in FIG. 11B, the slice position image 54 in FIG. 11A is pivoted in the y direction to obtain an orientation in FIG. 12A. When the joystick J is moved in the direction given by arrow 57 in FIG. 12B, the slice position image 54 is oriented as shown in FIG. 13A. Furthermore, when the joystick J is moved in the direction of arrow 58 in FIG. 13B, a display state shown in FIG. 14 is obtained. Now assume that the orientation of the slice position image is set as shown in FIG. 14. A slice is thus determined in accordance with this orientation.

In system processing, as shown in FIGS. 3A and 3B, the operator must operate the key input to confirm the selected slice. A desired slice may be two-dimensionally displayed as needed.

Scanning conditions of other slices are set, all the slices are confirmed, and the main routine of the system processing is ended. The scanning system 100 is operated in accordance with the set scanning conditions.

When a slice as an ROI is designated, elements to be displayed on the screen are line segments, points, a circular surface, a rectangular surface, a surface having any shape, or a combination thereof.

Display images are illustrated in FIGS. 15 to 20 when a slice is designated by other methods than the direct display technique described above.

Figure 15:
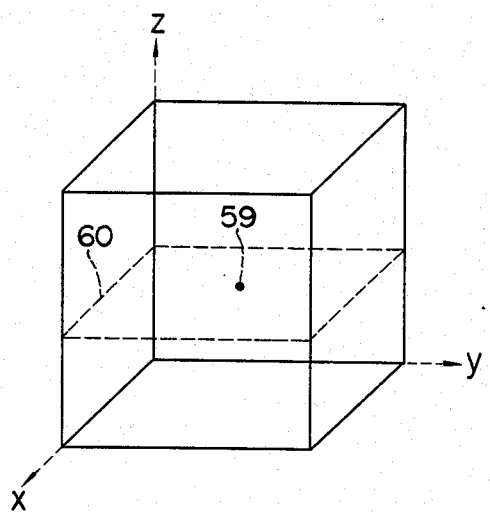
FIGS. 15 to 20 are, respectively, schematic representations of images displayed by various methods for designating a slice.

A single point is selected to designate an ROI, as shown in FIG. 15. When a three-dimensional coordinate system shown in FIG. 15 is considered, a plane 60 which includes a point 59 and is parallel to the x-y plane is designated as an ROI.

Figure 16:
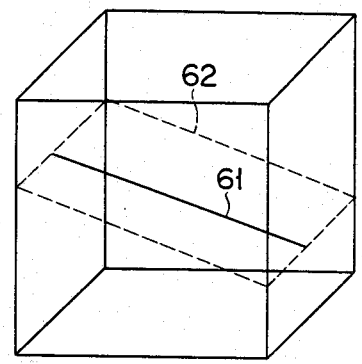

A line segment may be used to designate an ROI, as shown in FIG. 16. In this case, the ROI is given as a plane 62 which includes a line segment 61 and which is perpendicular to the y-z plane.

Figure 17A:
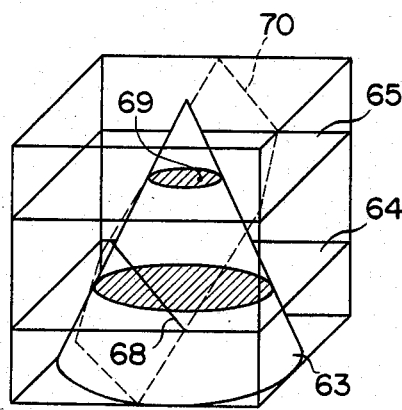
Figure 17B:
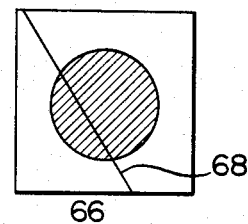
Figure 17C:
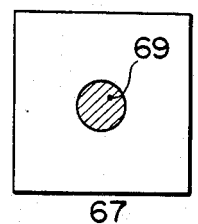
Figure 18:
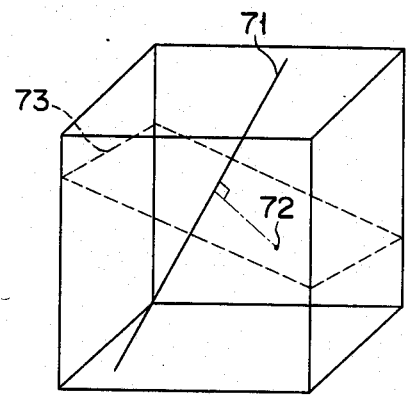

A combination of a line segment and a point may be used to designate an ROI, as shown in FIGS. 17A and 18. It is difficult to designate an ROI at a proper position by using only a point and a line segment in a three-dimensional coordinate system. In practice, the point and line segment are designated by using a two-dimensional image as an auxiliary figure. FIGS. 17A to 17C show a case wherein the point, the line segment and the auxiliary two-dimensional image are displayed. In this case, two slice position images 64 and 65 for the conical object image are displayed, and two-dimensional auxiliary slice images 66 and 67 are displayed to correspond to the planes 64 and 65, respectively, as shown in FIGS. 17B and 17C. A line segment 68 is designated by the image 66, and a point 69 is designated by the image 67. A plane defined by the line segment 68 and the point 69 is given as an ROI.

Another case will be illustrated in FIG. 18 wherein an ROI is designated by a point and a line segment as a rotational axis. A plane 73 perpendicular to this line segment, i.e., axis 71 and including a point 72, is defined as an ROI. This ROI designation is very effective in obtaining a plurality of parallel slices along a desired direction so as to provide an effective diagnostic tool.

Figure 19:
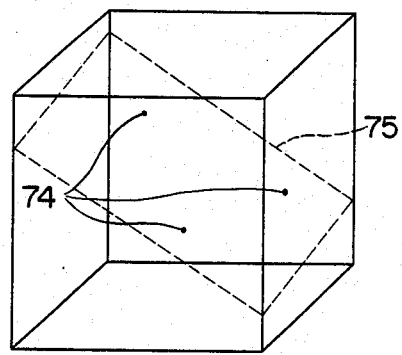
Figure 20:
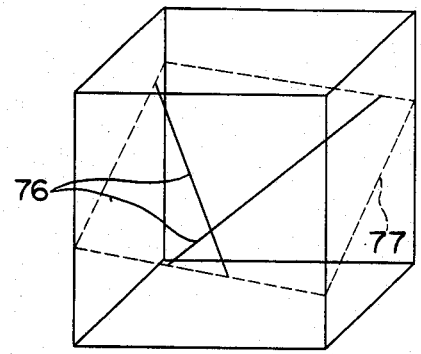

FIG. 19 shows a case wherein an ROI 75 is defined by three points 74a, 74b and 74c. FIG. 20 shows a case wherein an ROI 77 is defined by two crossing lines 76a and 76b.

Slice position images are also displayed in correspondence with the ROIs or slices, as shown in FIGS. 15 to 20, respectively. The operator is able to observe two-dimensional images defined by these slices as needed.

As has been described in detail according to the present invention, a three-dimensional object image is constructed by coarse data acquisition in the CT system, and the object image orientation is changed to allow the operator to observe from different viewpoints. Therefore, a more suitable slice can be selected. A slice position image displayed at the time of a slice selection is also three-dimensionally displayed. In addition, data inputs can be performed in a interactive manner, thereby decreasing the possibility of operational errors. According to the present invention, features of the MRI system for scanning any slice can be sufficiently utilized, and a clear tomographic image can be obtained instead of an unclear interpolated image. Therefore, according to the system of the present invention, the information supplied by the MRI system can be further improved. Furthermore, rescanning can be reduced so as to reduce the physical and mental strain on the patient. At the same time, the time spent by a doctor or an operator can be also reduced so as to contribute to a decrease in medical expense.

In the above description, the intervals between the parallel slices may be wide. The reason for this is that a possible slice selection range can be used to scan the slices in accordance with the three-dimensional display incorporating linear interpolation. In this sense, the intervals need not be increased. When a scanning system is used wherein slice pitches can be arbitrarily selected before the slice selection is designated, data acquisition may be performed at a large slice pitch.

The present invention is not limited to the MRI system but can be extended to different types of CT systems for scanning the slice at different angles.

What is claimed is:

1. A scan planning method for obtaining a tomographic image in a computed tomographic system, comprising:

a first process for acquiring, along different directions, projection data of a plurality of parallel slices of an object to be examined and for reconstructing a tomographic image of each of said plurality of parallel slices;

a second process including interpolating the plurality of tomographic images obtained by the first process and for obtaining three-dimensional image data of a region defined between two outermost slices of said plurality of parallel slices;

a third process for forming and displaying a three-dimensional object image in accordance with said three-dimensional image data obtained by the second process and for changing the viewpoint of said three-dimensional object image in accordance with externally entered first coordinate information;

a fourth process for superposing a slice position image on said three-dimensional object image displayed in the third process, said slice position image representing a slice position, and for changing the position and orientation of said slice on a screen in accordance with externally entered second coordinate information; and a fifth process for acquiring, along different directions, projection data of said slices corresponding to relative position information between said three-dimensional object image and said slice position image which are obtained in the third and fourth processes, and for reconstructing tomographic images of said respective slices.

2. A method according to claim 1, wherein said projection data is acquired to reconstruct said tomographic images by using common means in the first and fifth processes.

3. A method according to claim 1, wherein the second process comprises a process utilizing linear interpolation.

4. A method according to claim 1, wherein the second process includes a process for displaying an auxiliary line indicating the three-dimensional object image and the orientation thereof.

5. A method according to claim 1, wherein the fourth process includes a process for displaying said slice position image and a slice image defined by said slice position image by using said three-dimensional image data.

6. A method according to claim 1, wherein said position data obtained by the third and fourth processes are stored in memory means.

7. A scan planning apparatus for obtaining a tomographic image in a computed tomographic system, comprising:

a computed tomographic scanning system for acquiring, along different directions, projection data of predetermined slices of an object to be examined and for reconstructing tomographic images of said predetermined slices in accordance with said projection data;

first operating means for controlling said computed tomographic scanning system to cause said scanning system to acquire said projection data of said predetermined slices of said object along said different directions and to reconstruct tomographic images of said plurality of predetermined slices;

three-dimensional image forming means for interpolating said plurality of tomographic images by said first operating means, said plurality of tomographic images being obtained by said computed tomographic scanning system, and for forming three-dimensional image data of a region defined between two outermost slices of said plurality of predetermined slices;

image forming means for forming and displaying a three-dimensional object image in accordance with said three-dimensional image data obtained by said three-dimensional image forming means;

coordinate information input means for externally entering coordinate information;

viewpoint adjusting means, operated in association with said image forming means, for changing the viewpoint direction of said three-dimensional object image on a display screen in accordance with the coordinate information entered by said coordinate information input means;

slice setting means, operated in association with said viewpoint adjusting means, for forming and displaying a three-dimensional slice position image of a slice, the position and angle of which are variably adjusted in accordance with coordinate information, the three-dimensional slice position image being superposed on the image displayed by said image forming means in accordance with said coordinate information entered by said coordinate information input means, and for obtaining slice position information corresponding to the position and angle of said object image; and second operating means for controlling said scanning system to cause said scanning system to acquire projection data of the slice corresponding to said displayed slice position image in accordance with the slice position information set by said slice setting means, and for scanning the slice.

8. An apparatus according to claim 7, wherein said coordinate information input means has operation directivity such that an operating direction corresponds to a moving direction of the image moved by at least one of said viewpoint adjusting means and said slice setting means.

9. An apparatus according to claim 7, wherein said coordinate information input means comprises means including a track ball.

10. An apparatus according to claim 7, wherein said coordinate information input means comprises means including a three-dimensional joystick.

11. An apparatus according to claim 7, further comprising means for storing the slice position information which is obtained by said slice setting means and which corresponds to the plurality of slices, and for continuously supplying the slice position information to said second operating means.

12. An apparatus according to claim 7, wherein said computed tomographic scanning system comprises a magnetic resonance imaging system.

13. An apparatus according to claim 7, wherein said computed tomographic scanning system comprises an X-ray computed tomographic system.

14. An apparatus according to claim 7, wherein said computed tomographic scanning system comprises an emission computed tomographic system.

15. An apparatus according to claim 7, wherein said computed tomographic scanning system comprises an ultrasonic computed tomographic system.

* * * * *

UNITED STATES PATENT AND TRADEMARK OFFICE
CERTIFICATE OF CORRECTION

PATENT NO. : 4,674,046
DATED : June 16, 1987
INVENTOR(S) : Takeshi OZEKI, et al.

It is certified that error appears in the above-identified patent and that said Letters Patent is hereby corrected as shown below:

Page 1 of patent, the title should be changed as follows:

"projection slice data bind" to

--projection slice data and--

Signed and Sealed this

First Day of March, 1988

Attest:

DONALD J. QUIGG

Attesting Officer

Commissioner of Patents and Trademarks